United States Patent [19]
Heinemann et al.

[11] Patent Number: 5,291,884
[45] Date of Patent: Mar. 8, 1994

[54] APPARATUS FOR MEASURING A BLOOD PARAMETER

[75] Inventors: Stan O. Heinemann, Trabuco Canyon; Paul J. Mullin, Westminster; Susan Cavanaugh, San Clemente, all of Calif.

[73] Assignee: Minnesota Mining and Manufacturing Company, St. Paul, Minn.

[21] Appl. No.: 652,121

[22] Filed: Feb. 7, 1991

[51] Int. Cl.$^5$ .............................. A61B 5/00
[52] U.S. Cl. ...................... 128/633; 128/664; 128/665
[58] Field of Search .............. 128/633, 634, 664, 665; 356/40, 41

[56] References Cited

U.S. PATENT DOCUMENTS

| | | |
|---|---|---|
| 3,952,206 | 4/1976 | Liedholz . |
| 4,243,883 | 1/1981 | Schwarzmann . |
| 4,303,336 | 11/1981 | Cullis . |
| 4,305,659 | 12/1981 | Bilstad et al. . |
| 4,444,498 | 4/1984 | Heinemann . |
| 4,447,150 | 5/1984 | Heinemann . |
| 4,714,341 | 12/1987 | Hamaguri et al. . |
| 4,745,279 | 5/1988 | Karkar et al. . |
| 4,776,340 | 10/1988 | Moran et al. . |
| 4,800,885 | 1/1989 | Johnson . |
| 4,819,646 | 4/1989 | Cheung et al. . |
| 4,824,242 | 4/1989 | Frick et al. . |
| 4,846,183 | 7/1989 | Martin . |
| 4,925,299 | 5/1990 | Meisburger et al. ............ 356/40 |

FOREIGN PATENT DOCUMENTS

| | | |
|---|---|---|
| 0173155 | 3/1986 | European Pat. Off. . |
| 0316073 | 5/1989 | European Pat. Off. . |
| 3629447 | 4/1987 | Fed. Rep. of Germany . |
| 8606946 | 12/1986 | PCT Int'l Appl. . |

Primary Examiner—Randall L. Green
Assistant Examiner—A. Zuttarelli
Attorney, Agent, or Firm—Gordon L. Peterson

[57] ABSTRACT

An apparatus for measuring a blood parameter comprising a red light source and an infrared light source for directing light toward a blood-receiving location and a detector, for receiving light from the first and second light sources which has been back scattered by the blood. The intensity of the first light source is adjusted so that the intensity of light at the detector from the first light source remains substantially constant over a range of values of the blood parameter and the intensity of the second light source is adjusted so that the intensity of light at the detector from the second light source is substantially constant over a range of values of the blood parameter. A signal is provided which is related to the intensity of one or both of the light sources and which provides an indication of the blood parameter. A circuit is provided to compensate for errors resulting from the light sources.

17 Claims, 4 Drawing Sheets

APPARATUS FOR MEASURING A BLOOD PARAMETER

BACKGROUND OF THE INVENTION

It is sometimes necessary or desirable to measure various parameters of blood, such as hematocrit, oxygen saturation, carboxyhemoglobin, pH, etc. These blood parameters can all be measured using optical techniques.

For example, to measure oxygen saturation of whole blood, red light at, for example, 660 nanometers (nm) and infrared light at, for example, 805 nm are directed at the blood. The reflectance at both wavelengths is measured and appropriately ratioed to provide a measurement of oxygen saturation.

The hematocrit in whole blood may be measured, for example, by directing infrared light at the blood and detecting the reflectance of the infrared light at two spaced detectors. The hematocrit can then be determined by using a ratio of the two detected light levels or the difference between the two detected light levels. Another way to measure hematocrit is to employ a pair of spaced light sources and a single detector.

All of the techniques described above rely upon measuring of different detected light levels. Unfortunately, when the absorbance of the light directed at the blood is substantial, very low light levels are available for detection, and this results in a poor signal-to-noise ratio. In addition, when a constant level of light intensity is directed at the whole blood, the detected light level rises to a maximum near the middle of the physiologic range of hematocrit and then falls off this peak with increasing hematocrit levels. This curve creates an indeterminate condition in that it is not possible to determine which side of the peak is being observed so that an accurate hematocrit measurement is not obtainable.

Heinemann U.S. Pat. No. 4,447,150 discloses a technique for measurement of blood oxygen saturation which compensates for variations of hematocrit levels by assuring uniform depth of penetration of light into the blood being sampled. In this system, red and infrared light sources direct light toward a blood sample, and a single detector detects the light which is reflected or transmitted. Optical feedback from the detector is used to control the light emitted by one of the sources so that the light detected by the detector from such source is constant. The intensity of the light emitted from the second source is determined by a ratio between the current needed to drive the first source and the current needed to drive the second source. This latter technique does not establish the intensity of the second light source as accurately as may be desired. Also, this technique either suffers from inaccuracy resulting from inherent differences and drift between the light sources or it requires a matched set, which is more expensive to provide.

SUMMARY OF THE INVENTION

This invention provides a method and apparatus for measuring a blood parameter which generally overcomes the disadvantages noted above. According to this invention, optical feedback is used from a signal detector to each of the light sources being employed so that each of these sources can be more accurately controlled than in the prior art. In addition, this invention compensates for errors in the intensity of the light emitted by the light sources so as to provide improved accuracy without the need for matched sources.

One example of this invention is an apparatus for measuring hematocrit of whole blood. This apparatus includes a light source for emitting light toward a blood receiving location, a signal detector for receiving light from the light source after the emitted light interacts with the blood at the blood-receiving location, and a feedback loop. The feedback loop is responsive to the intensity of the light received by the signal detector to provide a feedback signal for adjusting the intensity of the light source so that the intensity of the light received by the signal detector is substantially constant over a range of values of the blood parameter. Means responsive to the feedback signal provides an output signal which provides an indication of the hematocrit. The feedback loop provides for accurate control of the light source.

Although a single light source emitting in the infrared range is suitable if the apparatus is only to detect hematocrit, to adapt the apparatus to measure other blood parameters, one or more additional light sources which emit light having appropriate wavelength characteristics, may also be employed. For example, to measure oxygen saturation, first and second light sources which emit light having first and second wavelength characteristics, respectively, are employed. A wavelength characteristic has reference to the wavelength or wavelengths which are suitable for measurement of the blood parameter of interest. For both hematocrit and oxygen saturation measurements, a narrow band is suitable. For example, one of these sources may emit red light of 660 nm and another of the sources may emit infrared light at 812 nm. Both of these light sources can be used for oxygen saturation measurements, and only the infrared source is required for hematocrit measurements.

Although multiple signal detectors can be employed, if desired, only a single detector is necessary, and a single detector is preferred for ratioing purposes. The signal detector receives light from the first and second light sources after interaction of the light with the blood at the blood-receiving location. This interaction may include transmission, reflection, diffusion, absorbance and/or back scattering of the light in the blood. Preferably, the signal detector receives substantially only light that has been reflected or back scattered, and optimally, only back-scattered light is received by the detector.

The intensity of the first light source is adjusted so that the intensity of the light at the signal detector from the first light source remains substantially constant over a range of values of the blood parameter. Similarly, the intensity of the light emitted by the second light source is adjusted so that the intensity of light at the signal detector from the second light source is also substantially constant over a range of values of the blood parameter. Thus, both the first and second light sources are controlled directly by the light intensity at the signal detector, and this provides greater control over the light sources and improved accuracy.

The apparatus also provides a signal which is related to the intensity of at least one of the first and second light sources and which provides an indication of the blood parameter of interest. For example, for hematocrit the signal may be a function of only one of the light intensities and not the other intensity. On the other hand, for oxygen saturation, the signal may be a function of the ratio of both of the light intensities.

The percent of oxygen saturation varies with hematocrit. To compensate for this effect which hematocrit has on oxygen saturation, the signal is preferably corrected for hematocrit so that the true oxygen saturation reading can be obtained.

The light intensity adjustments to maintain the desired emitted light levels from the first and second light sources can be accomplished in different ways. For example, this could be accomplished by appropriate attenuation of light intensity from strong light sources. However, preferably, this adjustment is accomplished by variably energizing the light sources. With this arrangement, the hematocrit or other blood parameter signal is related to the driving signal or current signal applied to the light source to generate the light intensity of the source.

The signal detector may provide a detector signal related to the intensity of the light received at the detector. The intensity adjustment may include a feedback loop responsive to the detector signal for providing a feedback signal to adjust the intensity of the light sources.

Ideally, the emitted light intensity varies or tracks with the feedback signal in accordance with a predetermined relationship. Preferably, this is a linear relationship. However, variables, such as nonlinearity of the light source with current input and temperature and aging of the light source make the emitted light intensity subject to deviating from, or not accurately tracking with, the predetermined relationship. Thus, there may be a difference between the light intensity commanded by the feedback signal and the light intensity actually emitted by the light source.

Another feature of this invention is to make the emitted light intensity more in accordance with the predetermined relationship, i.e., track more accurately with the feedback signal. This can be accomplished, for example, by producing a reference signal which is related, preferably linearly, to the light intensity actually emitted by the light source. The reference signal and the feedback signal are then used to control the light source to provide an emitted light intensity which is more in accordance with the predetermined relationship. Because this invention restores the relationship between the feedback signal and emitted light intensity, the feedback signal becomes an accurate variable to use as an output signal to provide an indication of the blood parameter of interest.

Although various techniques can be used for making the emitted light intensity more in accordance with the predetermined relationship, preferably the apparatus includes a reference detector for receiving at least some of the light emitted by the light source and circuit means responsive to the intensity of the light received by the reference detector for adjusting the intensity of the light emitted by the light source, i.e., to compensate the light source. The reference detector provides a reference detector signal which is related to the intensity of the light it receives. The circuit means receives the feedback signal and the reference detector signal and provides a driving signal to drive the light source to make the emitted light intensity more in accordance with the predetermined relationship. If the reference detector is a silicon diode, the relationship is linear.

The invention, together with additional features and advantages thereof, may best be understood by reference to the following description taken in connection with the accompanying illustrative drawings.

BRIEF DESCRIPTION OF THE DRAWING

FIG. 3 is a diagram showing system clock pulses and pulses generated in response to the clock pulses.

DESCRIPTION OF THE PREFERRED EMBODIMENT

Figure 1:
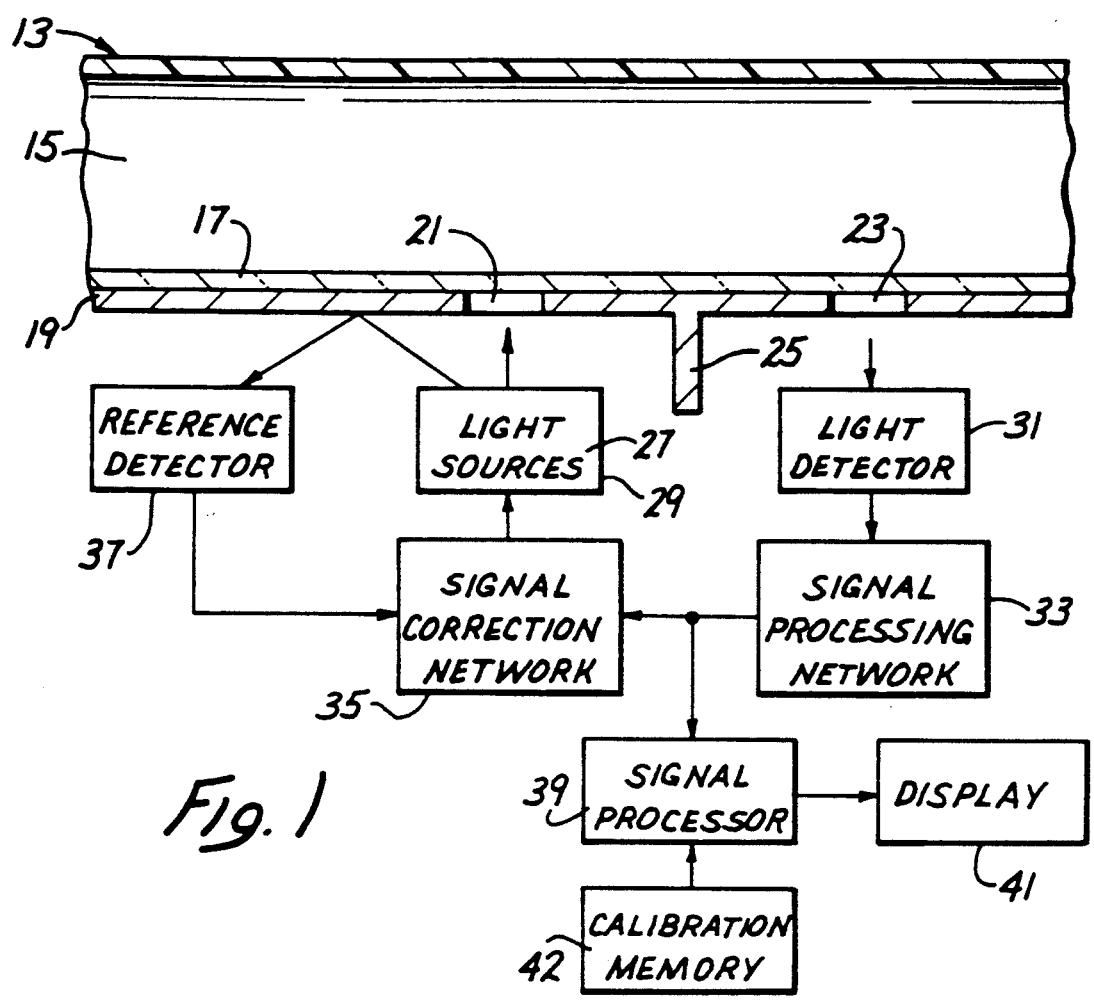
FIG. 1 is a schematic view illustrating one preferred form of the invention.

FIG. 1 shows an apparatus 11 which comprises an in-line flow-through housing 13 having a passage 15 extending therethrough and defining a blood-receiving location. The housing 13 is adapted to be coupled into a circuit, such as an extracorporeal circuit (not shown) of the type used in open-heart surgery. The apparatus 11 is adapted to measure hematocrit and oxygen saturation of whole blood in real time. Of course, the apparatus 11 can also be used to measure these blood parameters in a stationary blood sample.

The housing 13 includes a transparent window 17. An opaque cover 19 is suitably mounted, such as on the housing 13, contiguous the window 17. The cover 19 has a sending aperture 21 and a receiving aperture 23 spaced from the sending aperture. Except for an optical path through the window 17 and the passage 15, the apertures 21 and 23 are suitably optically isolated from each other as by an optical wall 25.

The apparatus 11 also includes a red light source 27 and an infrared light source 29 arranged to form point light sources on the axis of the sending aperture 21. The light sources 27 and 29, which may be light-emitting diodes, are arranged to be as close together as physically possible and are preferably pulsed using a short duty cycle to minimize self-heating of the LED.

The apparatus 11 also includes a light detector or signal detector 31 positioned on the axis of the receiving aperture 23 and adapted to provide a detected signal, such as a current signal, which is proportional to the intensity of the light detected by the detector. With this arrangement, the only light path from the sources 27 and 29 to the detector 31 is through the blood in the passage 15. The apertures 21 and 23 are preferably spaced so that substantially only back-scattered light, which has been back scattered by the blood in the passage 15, will reach the detector 31 from the sources 27 and 29. This spacing can be adjusted by those skilled in the art and may be, for example, from about 2.5 to about 3.5 mm between the axes of the apertures 21 and 23. Similarly, the spacing between the sources 27 and 29 and the aperture 21 can be varied depending upon the desired angle of emission of the emitted light from the sources. Preferably, the detector 31 and the light sources 27 and 29 are spaced equally from the associated apertures 21 and 23.

It is desirable to adjust the intensity of the light emitted by the light source 27 so that the intensity of the light at the detector 31 from the light source 27 remains substantially constant over a range of values of the blood parameters being measured. Similarly, the intensity of the light emitted by the light source 29 is also adjusted so that the intensity of the light at the detector 31 from the light source 29 is substantially constant over a range of values of the blood parameters being measured. Preferably, although not necessarily, the constant intensities of the sources are also known, predetermined values.

To control the intensity of the light sources 27 and 29, the detected signal from the light detector 31 is applied to a signal processing network 33 which provides a feedback signal which can be used to controllably drive the light sources 27 and 29. Although the feedback signal could be used directly to control the light sources, in this embodiment, the feedback signal is applied to a signal correction network 35.

Various factors, such as inherent nonlinearity of the light sources 27 and 29 and temperature and aging, can cause the light sources 27 and 29 to emit a light intensity different from the light intensity commanded by the feedback signal from the network 33. To make the emitted light intensity from the light sources 27 and 29 more in accordance with the correct or predetermined relationship between the feedback signal from the network 33 and the emitted light intensity, a reference detector 37 receives some of the light from the sources 27 and 29, such light being reflected from the cover 19. The reference detector 37 provides a reference detector signal to the signal correction network 35. The signal correction network 35 is responsive to the feedback signal and the reference detector signal to provide a driving signal to the light sources 27 and 29.

By alternately pulsing the light sources 27 and 29, the signal processing described above can be repeated until balance or equilibrium is reached for each of the light sources, i.e., until the intensity of the light detected at the detector 31 is constant at a desired intensity for each of the light sources. The feedback signals from the signal processing network 33 form output signals which are processed in a in a signal processor 39 to determine the values of the blood parameters being measured, and these values are displayed by a display 41.

When using the apparatus 11 with blood flowing through the passage 15, the process described above is run continuously to provide a real time display of the blood parameters being measured. In this embodiment, hematocrit is calculated as a function of the intensity of the infrared light source 29 after equilibrium has been reached. More specifically, the feedback signal from the signal processing network 33 resulting from operation of the infrared light source 29 after equilibrium has been reached is utilized by the signal processor 39 to calculate hematocrit in that hematocrit is proportional to that feedback signal.

Figure 6:
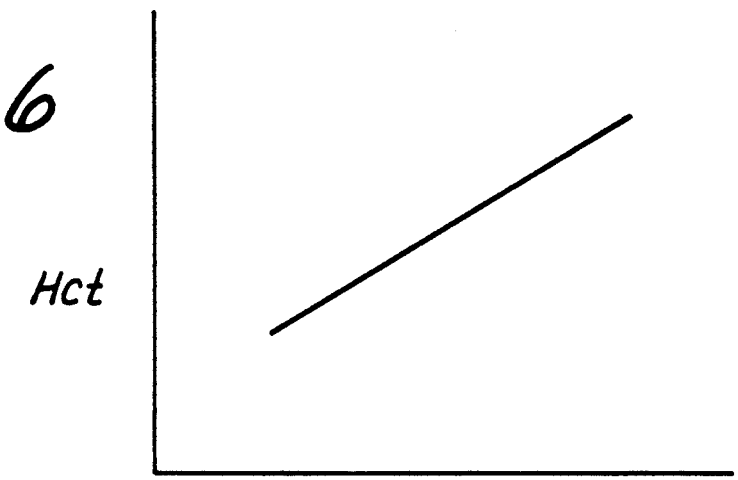
FIG. 6 is an exemplary plot of hematocrit versus the feedback signal from the infrared light source.

More specifically, the feedback signal derived from the infrared light source 29 is linearly related to hematocrit. The slope and offset of the linear relationship shown, by way of example in FIG. 6, is established during calibration and stored in a calibration memory 42 so that the curve of FIG. 6 can be established by the signal processor 39. With the curve of FIG. 6 established, the feedback signal derived from the infrared light source 29 establishes a point on the curve which represents the hematocrit. In terms of the usual straight-line equation, Hct=m(infrared feedback signal) + b where m is the slope of the curve shown in FIG. 6 and b is the offset from the X axis.

Oxygen saturation is determined by the signal processor 39 as 1 minus the ratio of the light intensities of the sources 27 and 29 at equilibrium. Specifically, the measured percent saturation equals 1 minus A/B where "A" is the intensity of the red light source 27 and "B" is the intensity of the infrared source 29. The feedback signals from the signal processing network 33 are used to represent the light intensities.

Figure 7:
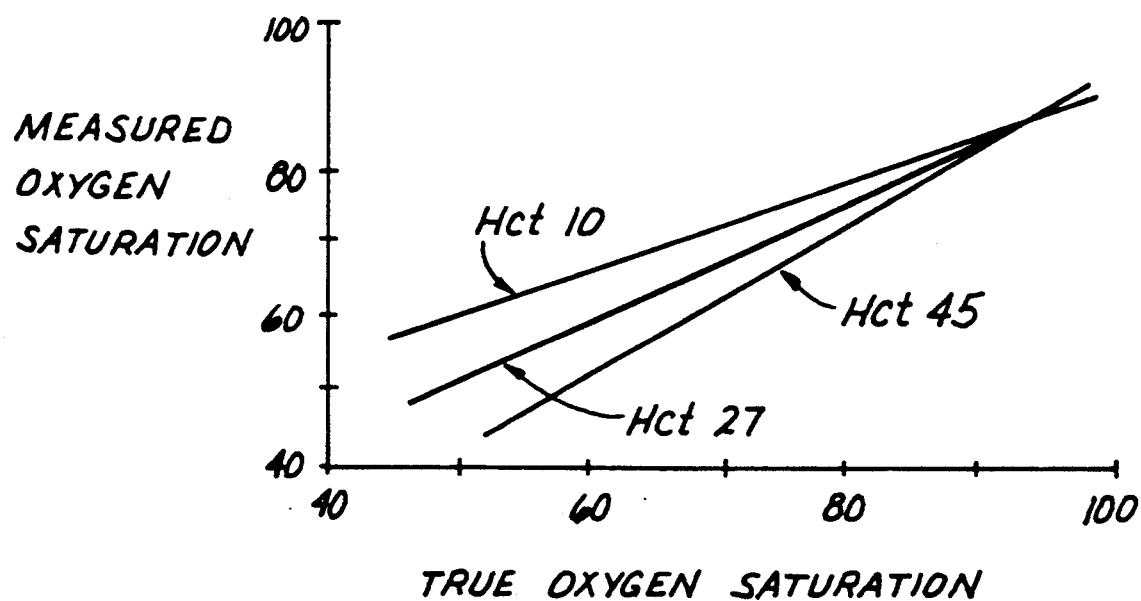
FIG. 7 is a family of plots showing how hematocrit affects the percent oxygen saturation.

For more accurate oxygen saturation results, the measured oxygen saturation should be corrected by a correction factor which is a function of the hematocrit. More specifically, the percent oxygen saturation as determined from the oxygen saturation formula set forth above is preferably corrected utilizing the family of curves shown in FIG. 7. Thus, by knowing the hematocrit, one curve of the family curves in FIG. 7 is selected so that the measured oxygen saturation can be corrected to yield a true oxygen saturation. FIG. 7 shows by way of example, oxygen saturation correction curves for only three values of hematocrit, but of course, a separate curve can be provided for as many hematocrit values as desired.

The curves of FIG. 7 can be established, for example, by empirical derivation during calibration. The correction factors represented by the family of curves can be stored in the calibration memory 42 and applied to the measured oxygen saturation by the signal processor 39 to result in the display 41 displaying the true oxygen saturation.

Figure 2:
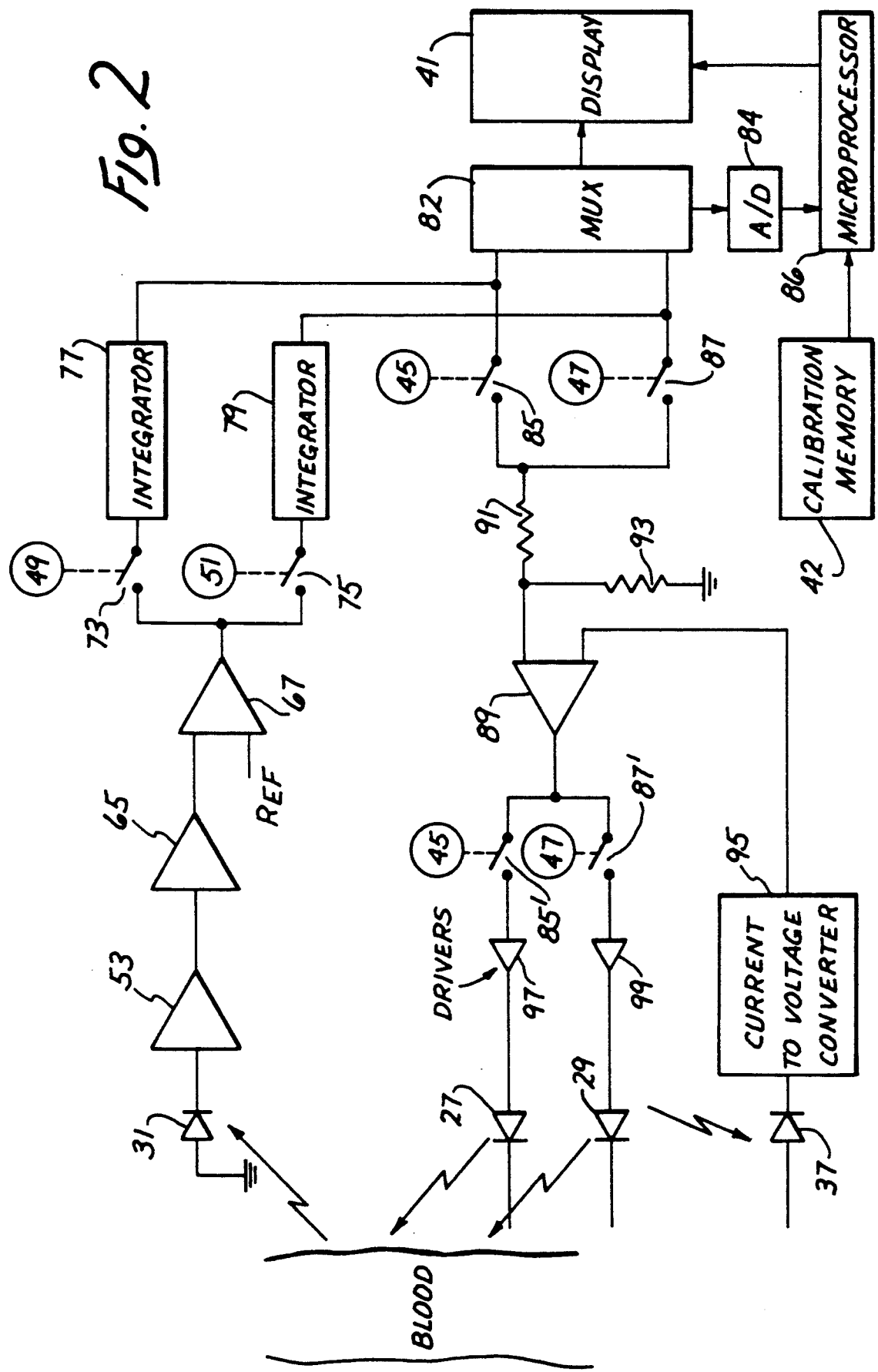
FIG. 2 is a more detailed schematic of the preferred form of the invention.

The signal processing network 33, the signal correction network 35 and the signal processor 39 can be implemented using a variety of analog and/or digital techniques. FIG. 2 shows one preferred way of implementing this circuit.

FIG. 2 can best be understood by first considering FIG. 3 which shows clock pulses 43 of the system clock. Derived from the clock pulses 43 are red emission pulses 45, infrared emission pulses 47, red switch pulses 49 and infrared switch pulses 51. By way of example, the pulses 45 have a duration of about 610 microseconds and are spaced by an interval of about 19.5 milliseconds. The infrared pulses 47 may have an identical duration and interval. As shown in FIG. 3, the pulses 45 and 47 occur alternately.

The switching pulses 49 and 51 are used to control switches as described below. The red switching pulse 49 occurs during the last half of each red emission pulse 45, and similarly, each of the infrared switching pulses 51 occurs during the last half of an associated infrared emission pulse 47. In this embodiment, intensity of the illumination of the sources 27 and 29 is controlled by changing the amplitude of the associated pulses 45 and 47. The interval between pulses remains fixed.

The light sources 27 and 29 emit light pulses in response to each of the pulses 45 and 47, respectively. Each of the light pulses is coextensive in time with the duration of the associated energizing emission pulse.

Figure 4A:
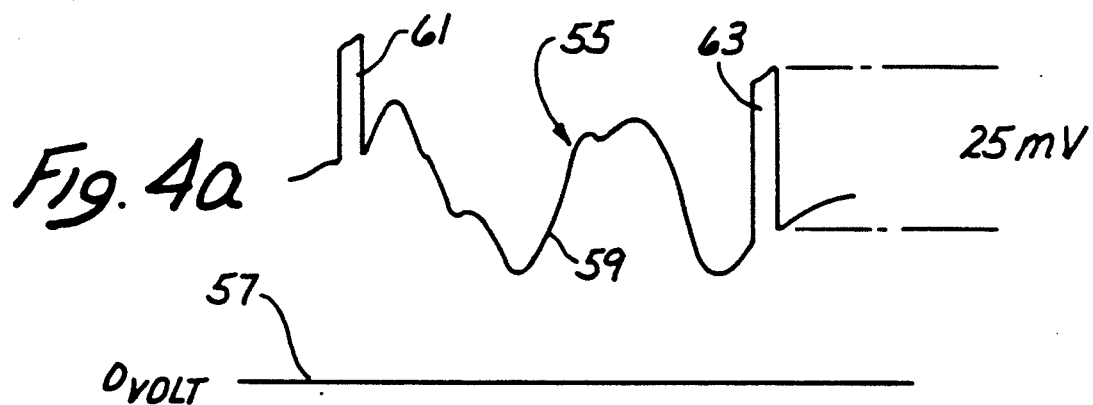
FIGS. 4a–4d show examples of signals occurring at various points in the circuit of FIG. 2.

The detector 31 provides a detected signal during each of the light pulses. The detected signal is amplified by an amplifier 53 (FIG. 2), and this provides a detected signal 55 at the output of the amplifier 53 as shown by way of example in FIG. 4a. The detected signal 55 has a dc level above a baseline 57 of zero volts which represents some of the ambient light seen by the detector 31 and a varying ac component 59 which represents variations in ambient light as seen by the detector. Superimposed on the ac component are detected pulses 61 and 63 which represent light from the light sources 27 and 29, respectively, resulting from one each of the emission pulses 45 and 47.

Figure 4B:
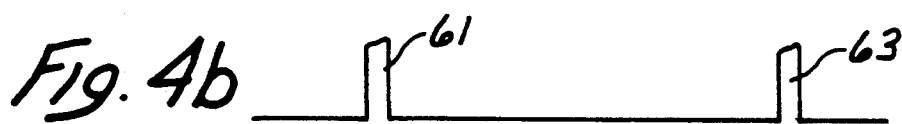

The detected signal 55 is applied to a filter and synchronous detector 65 which eliminates the dc component and noise and detects the signal component of the signal 55 to provide the detected pulses 61 and 63 as shown in FIG. 4b. If desired, the filter 65 may include an amplifier which amplifies the detected pulses 61 and 63 so that they may have an amplitude of, for example, about several volts.

Figure 4C:
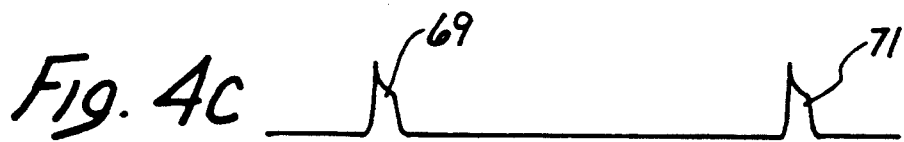

The detected pulses 61 and 63 are applied to one input of a comparator 67, which may be a voltage divider, and the other input of the comparator is coupled to a negative dc voltage reference. For each detected pulse 61 or 63, the output of the comparator 67 is a pulse having an amplitude equal to the algebraic sum of the positive detected pulse 61 or 63 and the negative dc reference. Assuming that the circuit is not in equilibrium, then the output of the comparator 67 is modified red pulses, 69 and modified infrared pulses 71 (FIG. 4c) which correspond to the pulses 61 and 63, respectively. The first half of each of the pulses 69 and 71 may be distorted as shown, by way of example, in FIG. 4c. Of course, with the circuit in equilibrium, there is a zero-volt output from the comparator 67.

The output of the comparator 67 is applied to a red selector switch 73 and an infrared selector switch 75. The switches 73 and 75, which may be field effect transistors, are normally open. However, the switches 73 and 75 are closed by an appropriate logic circuit during the red switch pulse 49 and the infrared switch pulse 51, respectively.

Figure 4D:
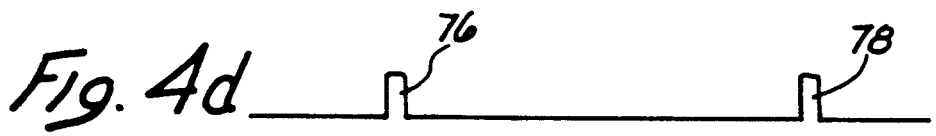

The effect of closing the switches 73 and 75 in this manner is twofold. First, because the switches 73 and 75 are closed only during the presence of associated modified pulses 69 and 71, they serve as a selector to apply the modified red pulse 69 to an integrator 77 and the modified infrared pulse 71 to another integrator 79. Second, because the switches 73 and 75 are closed only during the last half of the associated modified pulses 69 and 71, they serve to eliminate the distortion appearing in the first half of such pulse and provide shaped red pulses 76 and shaped infrared pulses 78,,respectively, (FIG. 4d).

Figure 5:
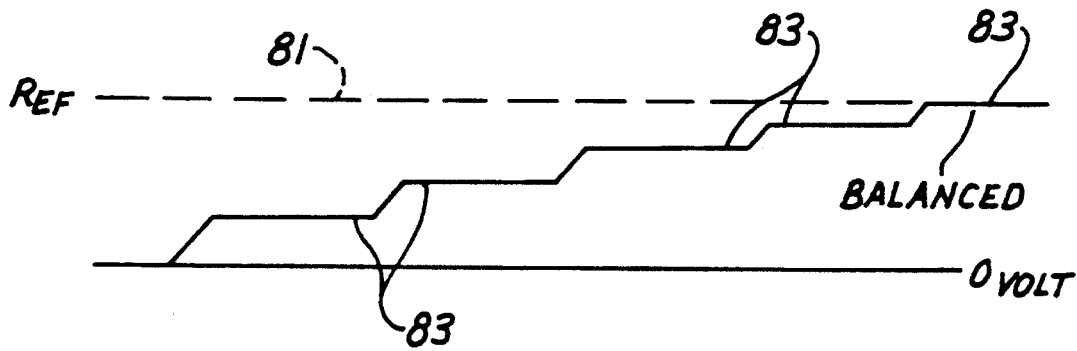
FIG. 5 shows one example of integrator output.

The number of integrators preferably equals the number of the light sources, and in this embodiment, two light sources 27 and 29 and two integrators 77 and 79 are provided. The integrators 77 and 79 are conventional analog integrators which integrate the shaped red pulses 76 and shaped infrared pulses 78, respectively. For example, the integrator 77 integrates a succession of the shaped red pulses 76 to provide an output which gradually approaches a desired output in stepwise fashion as shown by way of example in FIG. 5. FIG. 5 shows by way of example a voltage that is initially too low, thereby generating an illumination level at the source 27 which is too dim, and this may occur, for example, at startup. The desired illumination level is represented by a reference voltage level 81. In this example, each of the shaped red pulses 76 is of progressively increasing amplitude thereby resulting in a step-up in level of the output of the integrator 77 from a zero-volt baseline through a series of intermediate levels 83 until the reference voltage level 81 is reached. With each successive pulse 76 of increased amplitude, a new and higher intermediate level 83 is provided by the integrator as shown in FIG. 5. Typically, the incremental increases in intermediate voltage levels 83 are of progressively reducing magnitude as the reference voltage level is approached. The integrator 79 functions in the same manner with respect of the shaped infrared pulses 78.

The output of each of the integrators 77 and 79 constitutes a feedback signal which can be used to control the intensity of the light sources 27 and 29, respectively. The outputs of the integrators 77 and 79 are processed by the signal processor 39 which, in this embodiment, includes a multiplexer 82 for multiplexing the feedback signals resulting from the light sources 27 and 29, an A to D converter 84 for digitizing the multiplexed signals and a microprocessor 86 for performing the calculations discussed above to ascertain values for hematocrit and percent oxygen saturation. The microprocessor 86 also corrects the measured oxygen saturation for hematocrit to provide true oxygen saturation levels which, together with the hematocrit, are displayed by the display 41.

The outputs of the integrators 77 and 79 are applied to selector switches 85 and 87, which may be identical to the switches 73 and 75, respectively, and which are closed by conventional logic circuits in response to the pulses 45 and 47, respectively, in the same manner as described above for the switches 73 and 75. Thus, the switches 85 and 87 are closed only during the duration of the pulses 45 and 47, respectively.

The feedback signals from the integrators 77 and 79 are also applied through the switches 85 and 87, respectively, to one input of an operational amplifier 89 through a resistor 91. A junction between the resistor 91 and the amplifier 89 is coupled to ground through a resistor 93. The resistors 91 and 93 form a voltage divider. The other input of the operational amplifier 89 is coupled to the reference detector 37 through a conventional current-to-voltage converter 95. The reference detector 37 provides a reference detector signal, which is a current signal, which is linearly related to the intensity of the light emitted by the light source 27. The converter 95 converts this reference detector current signal to a reference detector voltage signal and provides the reference detector voltage signal to the other input of the operational amplifier 89. Accordingly, the amplifier 89 has as its inputs the feedback signal, which is commanding a particular light intensity, and the reference detector signal which represents actual intensity of the light source. Of course, the reference detector 37 also provides the reference detector signal in response to the light source 29 when that light source is energized.

The output of the operational amplifier 89 is a drive signal which the amplifier adjusts so as to attempt to obtain a reference detector signal which is equal to the feedback signal. The drive signal is applied to the appropriate one of the light sources 27 and 29 by selector switches 85' and 87' and drivers 97 and 99. The switches 85' and 87' are, like the switches 85 and 87, operated by the pulses 45 and 47, respectively so that the switches 85' and 87' are closed only during the duration of the pulses 45 and 47, respectively. In this manner, the drive signal from the amplifier 89, which is derived from the integrator 77 and the reference detector signal from the light source 27, is directed to the light source 27. Similarly, the appropriate drive signal for the light source 29 is directed to that light source.

With each pulse from the light source 27, the integrator 77 provides a feedback signal (FIG. 5) which is closer to the reference level 81. When the reference level is reached, the system is balanced and in equilibrium such that the feedback signal can be used for determination of the blood parameter of interest, such as hematocrit and the percent oxygen saturation. Similarly, the reference detector 37 and the resulting reference detector signal simultaneously correct for the variables caused by the light sources 27 and 29 such that the actual and commanded light intensities are substantially equal.

Although an exemplary embodiment of the invention has been shown and described, many changes, modifications and substitutions may be made by one having ordinary skill in the art without necessarily departing from the spirit and scope of this invention.

We claim:

1. An apparatus for measuring a blood parameter comprising:
    at least first and second light sources for emitting light having first and second light intensities, respectively, toward a blood-receiving location, the light emitted by said first and second light sources having first and second wavelength characteristics, respectively, said first and second wavelength characteristics being different;
    a detector for receiving light from the first and second light sources after interaction with blood at the blood-receiving location;
    means for adjusting the intensity of the light emitted by the first light source so that intensity of the light at the detector from the first light source is substantially constant over a range of values of the blood parameter and for adjusting the intensity of the light emitted by the second light source so that intensity of light at the detector from the second light source is substantially constant over a range of values of the blood parameter; and
    means for providing a signal which is related to the intensity of at least one of the first and second light sources and which provides an indication of the blood parameter.

2. An apparatus as defined in claim 1 wherein said signal is a function of the first light intensity and the blood parameter is hematocrit.

3. An apparatus as defined in claim 1 wherein said signal is a function of the first light intensity and not of the second light intensity and the blood parameter is hematocrit.

4. An apparatus as defined in claim 1 wherein the signal providing means provides a signal which is a function of the ratio of the first and second light intensities and the blood parameter is oxygen saturation.

5. An apparatus as defined in claim 1 wherein the detector provides a detector signal related to the intensity of the light received at the detector and the intensity adjusting means includes a feedback loop responsive to said detector signal for providing a feedback signal to adjust the intensities of the first and second light sources.

6. An apparatus as defined in claim 5 wherein the first intensity of the light emitted by the first light source is subject to varying for a given feedback signal to the first light source so that the first intensity does not accurately track with the feedback signal and said apparatus includes means for making the first intensity of the light emitted by the first light source track more accurately with said given feedback signal.

7. An apparatus as defined in claim 5 wherein the intensity of the light emitted by the first light source varies with the feedback signal in accordance with a predetermined relationship but is subject to deviating from said predetermined relationship and the apparatus includes means for reducing the deviations from said predetermined relationship.

8. An apparatus as defined in claim 1 including a reference detector for receiving at least some of the light emitted by the first light source and circuit means responsive to intensity of the light received by the reference detector for adjusting the intensity of the light emitted by the first light source.

9. An apparatus as defined in claim 5 including a reference detector for receiving at least some of the light emitted by the first light source and circuit means responsive to intensity of the light received by the reference detector and the feedback signal for adjusting the intensity of the light emitted by the first light source.

10. An apparatus as defined in claim 1 including a flow-through housing for blood defining said blood-receiving location.

11. An apparatus for measuring a blood parameter comprising:
    a light source for emitting light having an intensity toward a blood-receiving location;
    a detector for receiving light from the light source after the emitted light interacts with the blood at the blood-receiving location;
    a feedback loop responsive to intensity of the light received by the detector for providing a feedback signal for adjusting the intensity of the light source so that the intensity of the light received by the detector from the light source is substantially constant over a range of values of the blood parameter;
    said emitted light intensity varying with the feedback signal in accordance with a predetermined relationship and being subject to deviating from said relationship;
    a reference detector for receiving at least some of the light emitted by the light source and providing a reference detector signal which is related to the intensity of the light it receives;
    means responsive to the feedback signal and the reference detector signal for providing a drive signal for energizing the light source to make the emitted light intensity more in accordance with said relationship; and
    means responsive to the feedback signal for providing an output signal which provides an indication of the blood parameter.

12. An apparatus as defined in claim 11 wherein said blood parameter is hematocrit.

13. An apparatus as defined in claim 11 wherein the reference detector signal is linearly related to the intensity of the light it receives.

14. An apparatus as defined in claim 11 wherein said relationship is a linear relationship.

15. An apparatus as defined in claim 11 including a flow-through housing for blood defining said blood-receiving location.

16. An apparatus for measuring a blood parameter comprising:
    at least first and second light sources for emitting light having first and second light intensities, respectively, toward a blood-receiving location, the light emitted by the first and second light sources having first and second wavelength characteristics, respectively, said first and second wavelength characteristics being different;

a detector for receiving light from the first and second light sources after interaction with blood at the blood-receiving location;

a feedback loop for adjusting the intensity of the light emitted by the first light source so that intensity of the light at the detector from the first light source is substantially constant over a range of values of the blood parameter and for adjusting the intensity of the light emitted by the second light source so that intensity of light at the detector from the second light source is substantially constant over a range of values of the blood parameter; and a signal processor for providing a signal which is related to the intensity of at least one of the first and second light sources and which provides an indication of the blood parameter.

17. An apparatus for measuring a blood parameter comprising:

a light source for emitting light having an intensity toward a blood-receiving location;

a detector for receiving light from the light source after the emitted light interacts with the blood at the blood-receiving location;

a feedback loop responsive to intensity of the light received by the detector for providing a feedback signal for adjusting the intensity of the light source so that the intensity of the light received by the detector from the light source is substantially constant over a range of values of the blood parameter;

said emitted light intensity varying with the feedback signal in accordance with a predetermined relationship and being subject to deviating from said relationship;

a reference detector for receiving at least some of the light emitted by the light source and providing a reference detector signal which is related to the intensity of the light it receives;

a signal correction network responsive to the feedback signal and the reference detector signal for providing a drive signal for energizing the light source to make the emitted light intensity more in accordance with said relationship; and a signal processor responsive to the feedback signal for providing an output signal which provides an indication of the blood parameter.

* * * * *